United States Patent
Fritsch et al.

(10) Patent No.: US 10,790,047 B2
(45) Date of Patent: *Sep. 29, 2020

(54) COLLABORATIVE SYNTHESIS-BASED CLINICAL DOCUMENTATION

(71) Applicant: MModal IP LLC, Franklin, TN (US)

(72) Inventors: Juergen Fritsch, Pittsburgh, PA (US); Vasudevan Jagannathan, Morgantown, WV (US)

(73) Assignee: MModal IP LLC, Franklin, TN (US)

(*) Notice: Subject to any disclaimer, the term of this patent is extended or adjusted under 35 U.S.C. 154(b) by 184 days.

This patent is subject to a terminal disclaimer.

(21) Appl. No.: 14/217,945

(22) Filed: Mar. 18, 2014

(65) Prior Publication Data

US 2014/0304002 A1    Oct. 9, 2014

Related U.S. Application Data

(63) Continuation of application No. 14/208,950, filed on Mar. 13, 2014.

(Continued)

(51) Int. Cl.
G16H 10/60 (2018.01)
G16H 80/00 (2018.01)

(52) U.S. Cl.
CPC ............. *G16H 10/60* (2018.01); *G16H 80/00* (2018.01)

(58) Field of Classification Search
CPC ... G06F 19/322; G06F 19/3425; G06Q 50/24; G16H 40/20; G16H 10/06; G16H 40/63

(Continued)

(56) References Cited

U.S. PATENT DOCUMENTS 7,379,946 B2   5/2008  Carus
7,464,043 B1*  12/2008 Dussia ................. G06F 19/322
                                                128/900

(Continued)

FOREIGN PATENT DOCUMENTS

JP    2003131922    5/2003
JP    2010003082    1/2010

(Continued)

OTHER PUBLICATIONS

Final Rejection dated Oct. 22, 2018 for U.S. Appl. No. 14/208,950 of Juergen Fritsch, filed Mar. 13, 2014, 31 pages.

(Continued)

*Primary Examiner* — Hiep V Nguyen
(74) *Attorney, Agent, or Firm* — Blueshift IP, LLC; Robert Plotkin

(57) ABSTRACT

A graphical user interface, referred to herein as a virtual whiteboard, that provides both: (1) an automatically prioritized display of information related to a particular patient that is tailored to the current user of the system, and (2) a "scratch pad" area in which multiple users of the system may input free-form text and other data for sharing with other users of the system. When each user of the system accesses the virtual whiteboard, the system: (1) automatically prioritizes the patient information based on characteristics of the user and displays the automatically prioritized patient information to that user, and (2) displays the contents of the scratch pad to the user. As a result, the whiteboard displays both information that is tailored to the current user and information that is common to all users (i.e., not tailored to any particular user).

44 Claims, 9 Drawing Sheets

Related U.S. Application Data

(60) Provisional application No. 61/799,982, filed on Mar. 15, 2013.

(58) Field of Classification Search
USPC .............................................................. 705/3
See application file for complete search history.

(56) References Cited

U.S. PATENT DOCUMENTS

| | | | |
|---|---|---|---|
| 2002/0062229 A1* | 5/2002 | Alban | G06F 19/322 |
| | | | 705/3 |
| 2005/0015279 A1 | 1/2005 | Rucker | |
| 2006/0106645 A1* | 5/2006 | Bergelson | G06F 19/3425 |
| | | | 705/3 |
| 2006/0116908 A1 | 6/2006 | Dew | |
| 2007/0083403 A1* | 4/2007 | Baldwin | G06Q 10/10 |
| | | | 705/346 |
| 2008/0010087 A1 | 1/2008 | Daniel | |
| 2008/0065422 A1* | 3/2008 | Weber | G06Q 10/06 |
| | | | 705/3 |
| 2011/0112862 A1 | 5/2011 | Yu | |
| 2011/0301978 A1 | 12/2011 | Shiu | |
| 2012/0096091 A1 | 4/2012 | Miyama | |

FOREIGN PATENT DOCUMENTS

| | | |
|---|---|---|
| JP | 2011204055 | 10/2011 |
| WO | 2008057952 A2 | 5/2008 |

OTHER PUBLICATIONS

Decision to Refuse dated Oct. 16, 2018 in European Patent Application 14769020.0, 16 pages.
Provision of the minutes in accordance with Rule 124(4) EPC, issued Oct. 16, 2018 in European Patent Application 14769020.0, 4 pages.
Non-Final Rejection dated Apr. 15, 2019 for U.S. Appl. No. 14/208,950 of Juergen Fritsch, filed Mar. 13, 2014, 20 pages.

* cited by examiner

COLLABORATIVE SYNTHESIS-BASED CLINICAL DOCUMENTATION

BACKGROUND

Creating accurate and complete clinical documentation in the healthcare industry is fraught with difficulties for physicians and other healthcare providers. In particular, healthcare providers tend to have significant demands on their time, which often makes them dislike and resent the time required to produce clinical documentation, which disrupts their normal workflow and cuts into time they could spend providing healthcare services. Furthermore, modern healthcare providers have access to electronic health record (EHR) systems, which provide them with a collection of information that often is spread across many different screens, with significant duplication and clutter, and which provides significant amounts of detail while failing to provide a useful summary of the patient's current status and recent history. As a result, although EHR systems are intended to simplify the work of healthcare providers by providing all information about a particular patient and/or patient encounter in a single database, deficiencies in the implementations of such systems often make them fall far short of their promise to simplify the work of healthcare providers. Due to the difficulty of using EHR systems to quickly and easily locate and digest all of the most relevant and recent information about a particular patient, healthcare providers often choose to resort to manual and low-tech methods for recording and retrieving such information, such as writing lengthy notes, often on paper, that detail the current status, problems, medications, and recent history of the patient, after each patient encounter. In writing such notes (whether on paper or using a computer), healthcare providers often copy information from previous notes and/or from EHR records into the current note, to make that note usable as a summary of the most important and relevant information for the next healthcare provider in the patient encounter to know. Not only is the process of writing such detailed notes after each encounter time-consuming and inefficient, the process of passing such notes from one healthcare provider to another is fraught with opportunities for errors (such as incorrect copying of information and failure to include relevant information) and for loss of the notes themselves. Although providing quality healthcare services requires the many healthcare providers who are involved in providing such services to a particular patient in a particular encounter to share information about the patient with each other smoothly and accurately, modern EHR systems fail to facilitate such a process.

Furthermore, modern EHR systems are designed and implemented to capture documentation of patient encounters in ways that are suitable for enabling reimbursement to be obtained for such services. Engineering EHR systems with a focus on reimbursement for services tends to result in a failure to provide features that facilitate collaboration and communication among healthcare providers, because such features are not strictly necessary to enable proper reimbursement to be obtained.

As the conditions of the healthcare industry continue to push healthcare providers to provide care that is both increasingly efficient and of increasingly high quality, the deficiencies in existing EHR systems are having increasingly negative impacts on healthcare providers, particularly because the documentation produced by such systems is becoming less and less useful as a practical tool for healthcare providers to use in the provision of healthcare services, especially services which require a team of healthcare providers to collaborate with each other over time to provide an array of services to a patient over the course of a particular encounter.

SUMMARY

Embodiments of the present invention provide healthcare providers with a graphical user interface, referred to herein as a virtual whiteboard, that provides both: (1) an automatically prioritized display of information related to a particular patient that is tailored to the current user of the system, and (2) an area, referred to herein as a "scratch pad," in which multiple users of the system may input free-form text and other data for sharing with other users of the system. When each user of the system accesses the virtual whiteboard, the system: (1) automatically prioritizes the patient information based on characteristics of the user and displays the automatically prioritized patient information to that user, and (2) displays the contents of the scratch pad to the user. As a result, the whiteboard displays both information that is tailored to the current user and information that is common to all users (i.e., not tailored to any particular user). The system thereby serves as a mechanism both for enabling users to obtain quick and easy access to relevant patient information from sources such as Electronic Health Records (EHRs) and as a tool for informal communication among members of the team responsible for providing healthcare services in connection with a particular patient encounter.

Other features and advantages of various aspects and embodiments of the present invention will become apparent from the following description and from the claims.

DETAILED DESCRIPTION

Embodiments of the present invention provide healthcare providers with a graphical user interface, referred to herein as a virtual whiteboard, that provides both: (1) an automatically prioritized display of information related to a particular patient that is tailored to the current user of the system, and (2) an area, referred to herein as a "scratch pad," in which multiple users of the system may input free-form text and other data for sharing with other users of the system. When each user of the system accesses the virtual whiteboard, the system: (1) automatically prioritizes the patient information based on characteristics of the user and displays the automatically prioritized patient information to that user, and (2) displays the contents of the scratch pad to the user. As a result, the whiteboard displays both information that is tailored to the current user and information that is common to all users (i.e., not tailored to any particular user). The system thereby serves as a mechanism both for enabling users to obtain quick and easy access to relevant patient information from sources such as Electronic Health Records (EHRs) and as a tool for informal communication among members of the team responsible for providing healthcare services in connection with a particular patient encounter.

Figure 1:
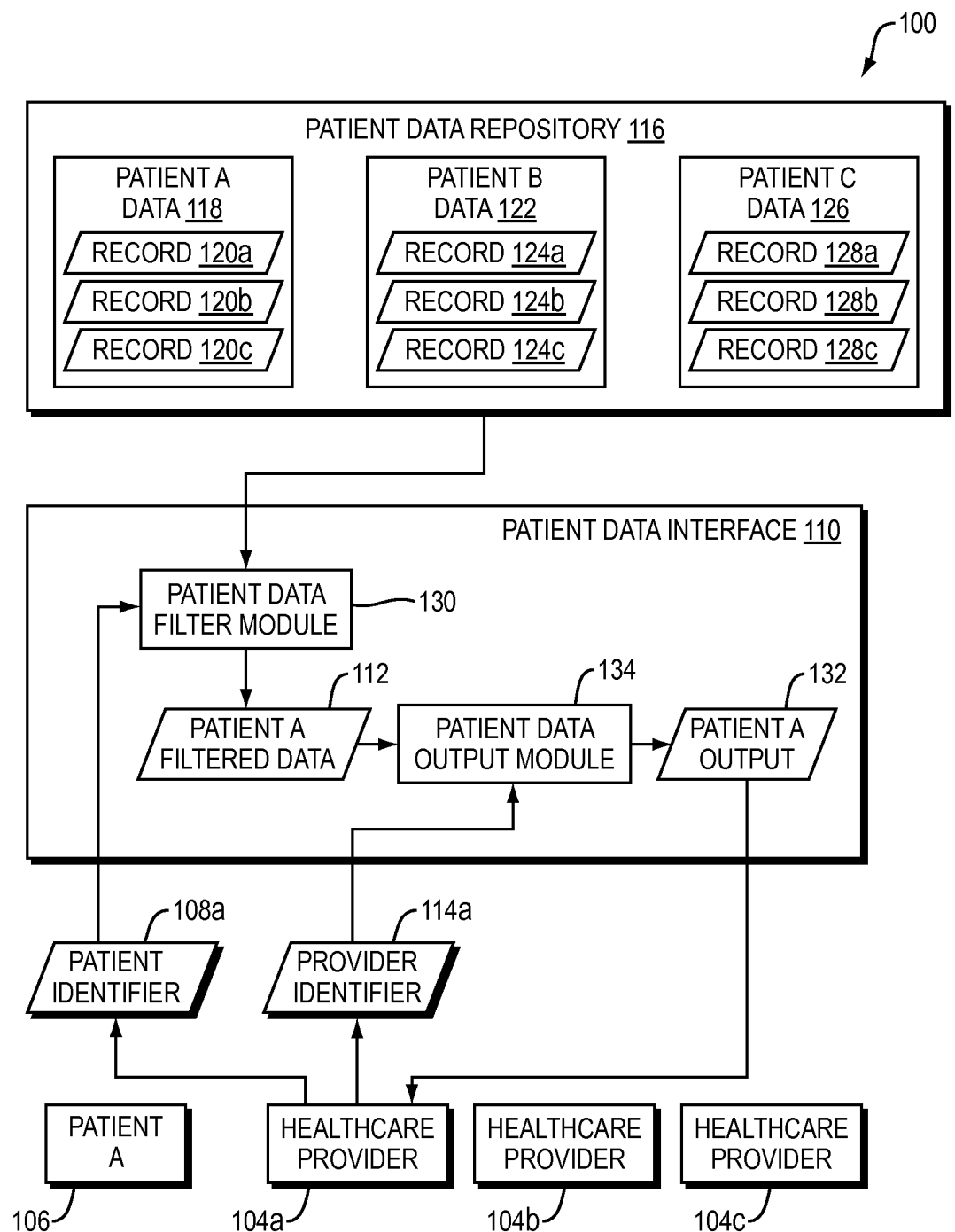
FIG. 1 is a dataflow diagram of a system for providing an interactive summary of relevant patient information according to one embodiment of the present invention.
Figure 2:
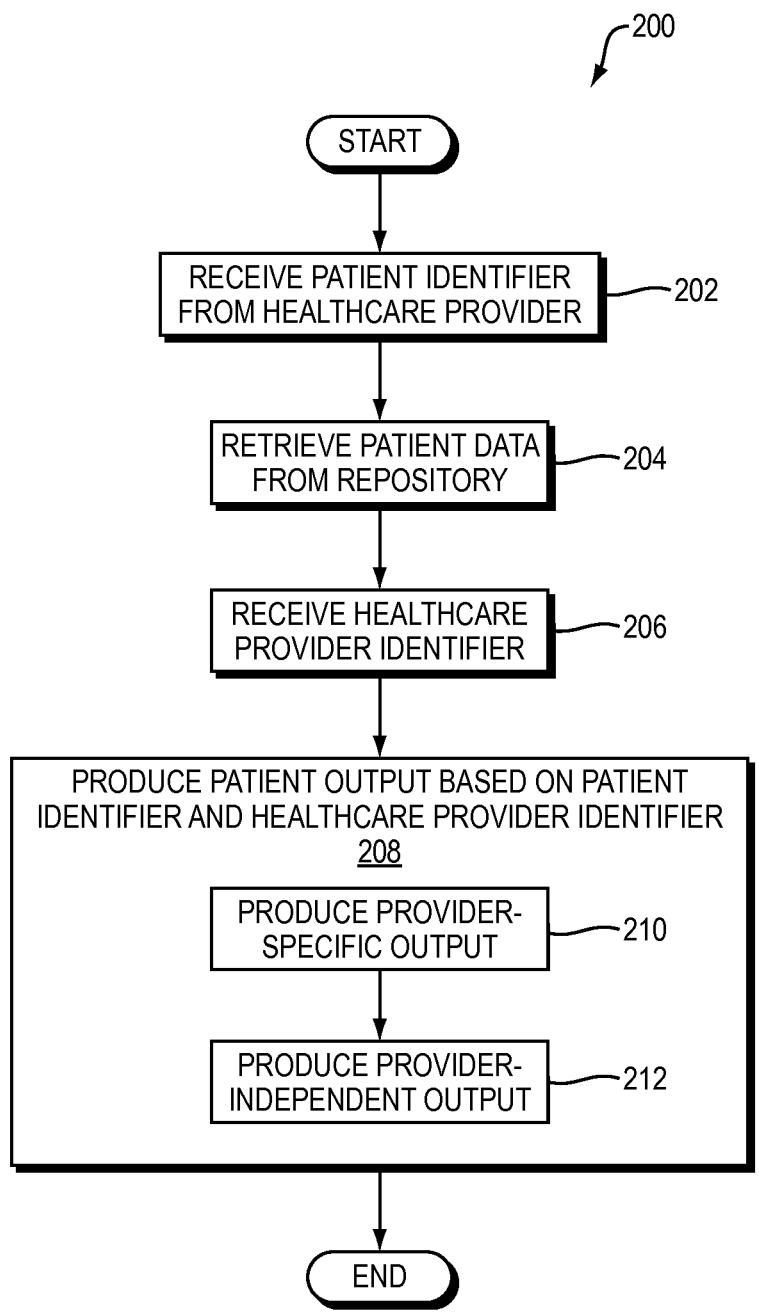
FIG. 2 is a flowchart of a method performed by the system of FIG. 1 according to one embodiment of the present invention.

For example, referring to FIG. 1, a dataflow diagram is shown of a system 100 for providing an interactive summary of relevant patient information to a plurality of healthcare providers 104a-c according to one embodiment of the present invention. Referring to FIG. 2, a flowchart is shown of a method 200 performed by the system 100 of FIG. 1 according to one embodiment of the present invention.

The healthcare providers 104a-c may, for example, be a team of healthcare providers responsible for or otherwise involved in providing healthcare services to a patient 106 in connection with one or more encounters of the patient, such as any combination of doctors, nurses, physical therapists, and billing coding specialists. Even more generally, embodiments of the present invention may be used in fields other than healthcare. As a result, the healthcare providers 104a-c may more generally be any users who are responsible for providing services to the patient 106 or other person. Although three healthcare providers 104a-c are shown in FIG. 1 for purposes of example, the techniques disclosed herein may be applied in connection with any number of healthcare providers.

The patient 106's "encounter" may include, for example, one or more of each of the following in any combination: an examination, a hospital stay, a medical procedure, and an appointment. As mentioned above, the system 100 may be used to provide the healthcare providers 104a-c with information that is relevant to one or more encounters of the patient 106.

The system 100 includes a patient data repository 116. The repository 116 may include any one or more of the following: electronic health records (EHRs) of the patient 106 and of other patients, clinical notes related to the patient 106 and to other patients, other documents (such as unstructured and/or structured documents) related to the patient 106 and to other patients, bills related to the patient 106 and other patients, and any other data (such as documents and/or database records) related to the patient 106 and other patients. Documents and other data stored in the repository 116 may include structured documents of the kind produced using the techniques disclosed in the above-referenced U.S. Pat. Nos. 7,584,103 and 7,716,040, and may therefore include encoded concepts. Although the patient data repository 116 is shown in FIG. 1 as a single data store for ease of illustration, in practice the patient data repository 116 may be implemented as multiple data stores which may be distributed in any manner.

For purposes of example, the patient data repository 116 is shown in FIG. 1A as containing:
- data 118 relating to patient 106, including records 120a, 120b, and 120c;
- data 122 relating to a first patient (not shown) other than patient 106, including records 124a, 124b, and 124c; and
- data 126 relating to a second patient (not shown) other than patient 106, including records 128a, 128b, and 128c.

The particular numbers of patient data records 120a-c, 124a-c, and 128a-c shown in FIG. 1A are merely examples and do not constitute limitations of the present invention. Each of the data records 120a-c, 124a-c, and 128a-c may be of any of the types disclosed herein (e.g., EHR, clinical note) in any combination.

Now consider a situation in which the healthcare provider 104a desires to view and/or edit information related to an encounter of the patient 106. To initiate such a session, the healthcare provider 104a may provide input 108a representing an identifier of the patient 106, such as a name, social security number, or other identifier of the patient 106. The system 100 includes a patient data interface 110, which receives the patient identifier 108a (FIG. 2, operation 202).

The patient data interface 110 may, for example, be integrated into or communicate with an existing EHR system. The patient data interface 110 may include a patient data filter module 130, which may receive the patient identifier 108a and, in in response, retrieve some or all of the patient 106's data 118 from the repository 116 (FIG. 2, operation 204). The filter module 130 may use the patient identifier 108a to identify data 118 related to the patient 106, such as by using the identifier to query the repository 116 or as an index into the repository 116.

The patient data filter module 130 may filter and/or otherwise process such data 118 to produce filtered data 112. Alternatively, however, the filter module 130 may include all of the patient data 118 in the filtered data 112 without filtering and/or otherwise processing such data 118.

The healthcare provider 104a may also provide input 114a representing an identifier of the healthcare provider 104a. The patient data interface 110 may receive the healthcare provider identifier 114a (FIG. 2, operation 206). The healthcare provider identifier 114a may include any of a variety of information, such as one or more of the following: a real name of the healthcare provider 104a, a username and/or password of the healthcare provider 104a (such as a username and/or password of the healthcare provider 104a for an EHR system), a practice area of the healthcare provider 104a (e.g., cardiology, orthopedics, or internal medicine), and a role of the healthcare provider 104a in the current encounter of the patient 106. The patient data interface 110 may receive some or all of the healthcare provider identifier 114a from a source other than the healthcare provider 104a. For example, the patient data interface 110 may receive some or all of the healthcare provider identifier 114a (such as the medical practice area and/or role of the healthcare provider 104) from an EHR system or other computer system.

The patient data interface 110 also includes a patient data output module 134, which receives the patient data 112 and the provider identifier 114a and, based on the patient data 112 and the provider identifier 114a, produces patient output 132 and provides the output 132 to the healthcare provider 104a (FIG. 2, operation 208). The patient data output module 134 may produce the patient output 132 based on the patient data 112 and the provider identifier 114a in any of a variety of ways. In general, the patient data output module 134 may modify the patient data 112 based on the provider identifier 114a, such as by performing any one or more of the following operations: prioritizing (e.g., re-ordering) data within the patient data 112 based on the provider identifier 114a, summarizing data within the patient data 112 to produce summary data based on the provider identifier 114a, and filtering (removing) data from the patient data 112 based on the provider identifier 114a. For example, the patient data output module 134 may perform such operations on the patient data 112 to produce output 132 which is tailored to one or more characteristics of the healthcare provider 104a, such as the medical practice field and/or role of the healthcare provider 104a. For example, if the healthcare provider 104a is a cardiologist, the output 132 may represent a presentation of the patient data 112 which is tailored to emphasize the data within the patient data 112 that are most relevant to a cardiologist.

Figure 3:
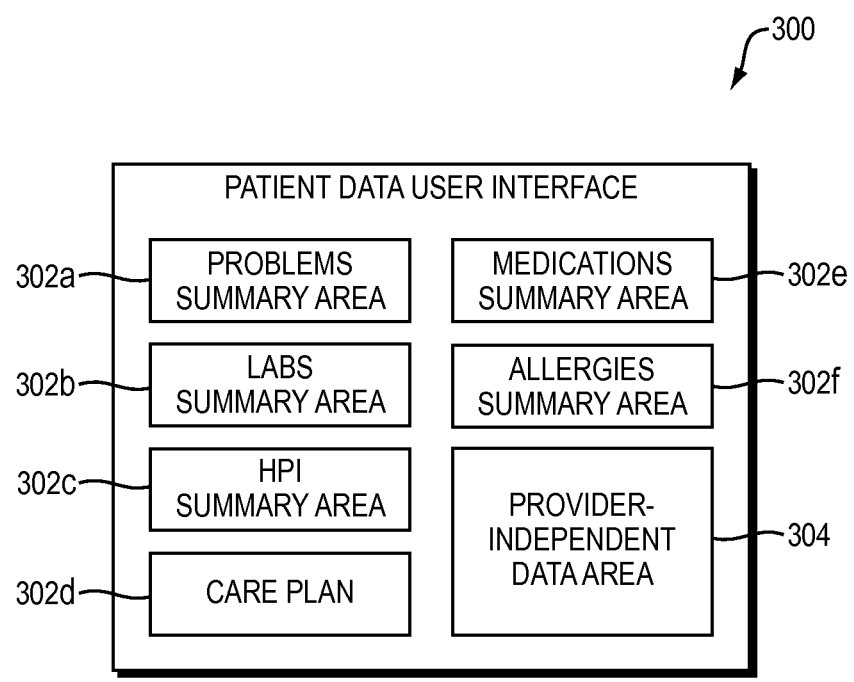
FIG. 3 is an illustration of a graphical user interface for displaying relevant patient information according to one embodiment of the present invention.

In general the output 132 may take any form that represents the result of the processing performed by the patient data output module 134. Referring to FIG. 3, an illustration is shown of the structure of a graphical user interface 300 that is used to implement the patient output 132 according to one embodiment of the present invention. The user interface 300 includes a plurality of areas 302a-f, each of which displays corresponding data in the patient output 132. The particular number, types, and arrangement of the areas 302a-f in FIG. 3 are merely examples and do not constitute limitations of the present invention. In particular, the areas 302a-f include:

a problems summary area 302a, which displays data representing a summary of the patient 106's current problems;

a labs summary area 302b, which displays data representing a summary of the patient 106's laboratory results;

an HPI (history of the present illness) summary area 302c, which displays a history of the patient 106's present illness;

a care plan area 302d, which displays data representing a care plan of the patient 106;

a medications summary area 302e, which displays data representing the patient 106's current and/or past medications; and an allergies summary area 302f, which displays data representing the patient 106's allergies.

Each of the areas 302a-f may, for example, display data corresponding to one of the records 120a-c in the patient 106'a data 118 in the repository 116. For example, the problems summary area 302a may display data corresponding to (and derived from) a problems summary record in the data 118 in the repository 116, and the labs summary area 302b may display data corresponding to (and derived from) a labs summary record in the data 118 in the repository.

FIG. 3 merely illustrates an overall layout and high-level structure of the user interface 300. The user interface 300 may further represent the prioritization of the data within the output 132 in a variety of ways. For example:

if the patient data output module 134 re-ordered data within the problems summary section of the patient data 112 to produce a re-ordered version of the problems summary section in the patient output 132, then the problems summary section 302a may display the data in the problems summary section in the order produced by the patient data output module 134;

if the patient data output module 134 summarized data within the problems summary section of the patient data 112 to produce a summarized version of the problems summary section in the patient output 132, then the problems summary section 302a may display the summarized version of the problems summary section;

if the patient data output module 134 removed data from the problems summary section of the patient data 112 to produce a filtered version of the problems summary section in the patient output 132, then the problems summary section 302a may display the filtered version of the problems summary section; and if the patient data output module 134 emphasized data within the problems summary section of the patient data 112 (such as by changing any one or more of the color, font, font size, font characteristics (e.g., bold, underline, italics), or location of such data) to produce an emphasized version of the problems summary section in the patient output 132, then the problems summary section 302a may display the summarized version of the problems summary section.

The patient data output module 134 may perform any one or more of the operations described above on the patient data 112 to produce the patient output 132. Furthermore, such operations may be performed to render any one or more of the areas 302a-f.

As another example, the patient data 112 may include data having a hierarchical structure, such as a problems list which include problems and sub-problems of those problems. The patient output 132 may reflect such a hierarchical structure, such as by rendering some or all of the patient data 112 in a manner that reflects the data 112's hierarchical structure within the corresponding areas 302a-f. For example, the problems summary area 302a may be rendered to display the patient 106a's problems summary in a hierarchical (e.g., tree) structure. Such a hierarchical display may be collapsible and/or expandable. For example, the hierarchical display may display certain nodes in the hierarchy but not sub-nodes of those nodes. The output module 134 may, however, display the sub-nodes of a node (i.e., expand the node) in response to input from the healthcare provider 104a. For example, the user interface 300 may display a plus sign next to the representation of the node. The healthcare provider 104a may click on or otherwise select the plus sign, in response to which the output module 134 may modify the output 132 by displaying the sub-nodes of the selected node. The user interface 300 may, for example, display a minus sign next to a node for which sub-nodes are displayed. To collapse the node (i.e., to hide the sub-nodes of the node), the healthcare provider 104a may click on or otherwise select the minus sign, in response to which the output module 134 may modify the output 132 by hiding the sub-nodes of the selected node.

Producing the initial display of the output 132 (in operation 208 of FIG. 2) may include collapsing one or more nodes of data in the patient data 112 to de-emphasize such nodes if such nodes are determined by the output module 134 to be of insufficient relevance to the healthcare provider 104a, and/or expanding one or more nodes of data in the patient data 112 to emphasize such nodes if such nodes are determined by the output module 134 to be of sufficient relevance to the healthcare provider 104a.

In general, the output module 134 may apply a relevance criterion to each of one or more portions P of the patient data 112 to determine whether the portion P satisfies the relevance criterion. The output module 134 may select the relevance criterion based on the identifier 114a (e.g., medical practice area and/or role) of the healthcare provider 104a. As this implies the output module 134 may apply different relevance criteria to different healthcare providers 104a-c based on differences in their provider identifiers 114a-c. The output module 134 may perform any of the operations described herein on the patient data 112 (e.g., prioritizing, emphasizing, and/or filtering such data 112) to produce the output 132.

In summary, therefore, the patient data interface 110 may provide output 132 (e.g., the user interface 300) that represents some or all of the patient data 112 in a manner that is tailored to the specific healthcare provider to whom the output 132 is provided. As this implies, other healthcare providers 104b and 104c may provider their own identifiers (not shown) to the patient data interface 110, in response to which the patient data interface 110 may perform operations 202-208, to thereby produce alternate versions of patient output 132 which are tailored to the other healthcare providers 104b-c. For example, in response to receiving the identifier of healthcare provider 104b, the patient data interface 110 may perform operations 202-208, and thereby produce an alternate version of patient output 132 which is tailored to the healthcare provider 104b based on healthcare provider 104b's identifier. Such alternate output may, for example, be implemented using an instance of the user interface 300 which has the same structure as that shown in FIG. 3, but in which the contents of the fields 302a-f differ from the contents displayed to the healthcare provider 104a, even if such contents were derived from the same patient data 112. The differences in the contents of the user interface 300 provided to healthcare provider 104a and the contents of the user interface 300 provided to healthcare provider 104b may be based, for example, on a difference in the medical practice field and/or role of the healthcare providers 104a and 104b. For example, the patient data interface 110 may provide a first version of the user interface 300 to the healthcare provider 104a that is tailored to cardiologists (assuming that the healthcare provider 104a is a cardiologist), while the patient data interface 110 may provide a second version of the user interface 300 to the healthcare provider 104b that is tailored to orthopedists (assuming that the healthcare provider 104b is an orthopedist).

The output 132 may also include data, referred to herein as "common data" or "provider-independent data" that is provided to some or all of the healthcare providers 104a-c as part of the output 132. For example, the output 132 may include both: (1) provider-specific data that is generated by the output module 134 based on the identifier (e.g., identifier 114a) of the provider (e.g., provider 104a) to whom the output 132 is displayed; and (2) provider-independent data, which is generated by the output module 134 independently of the identifier (e.g., identifier 114a) of the provider (e.g., provider 104a) to whom output 132 is displayed. For example, as shown in FIG. 2, the output module 134 may produce output 132 in operation 208 by generating both provider-specific output (FIG. 2, operation 210) and provider-independent output (FIG. 2, operation 212). Although the output 132 is provider-independent, it is still specific to the patient 106 and/or to the current encounter of the patient 106. In the example user interface 300 of FIG. 3, the scratchpad area 304 may display information representing the provider-independent data in the patient output 132.

Figure 4:
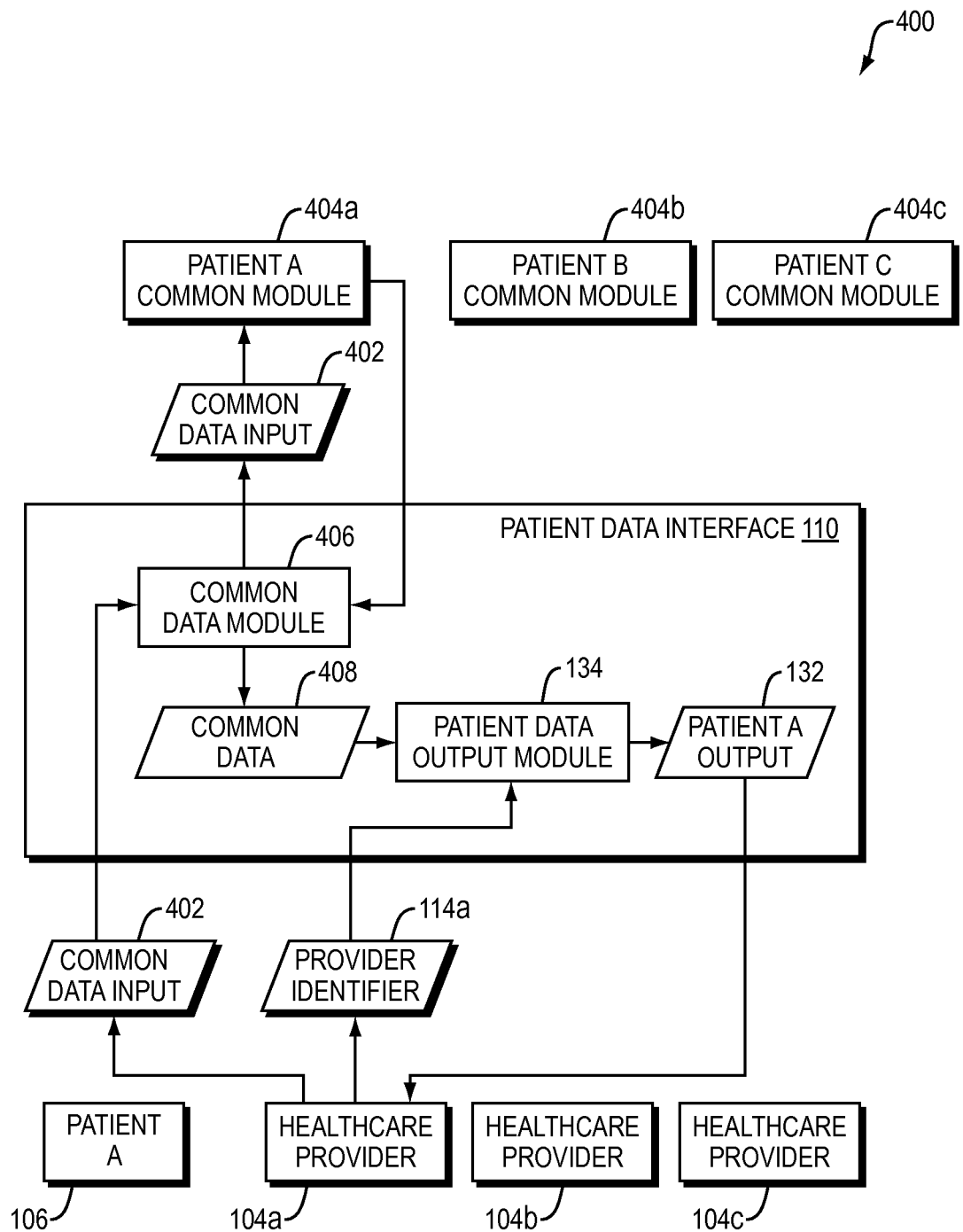
FIG. 4 is a dataflow diagram of a system for receiving and displaying patient data that is common to a plurality of healthcare providers according to one embodiment of the present invention.
Figure 5:
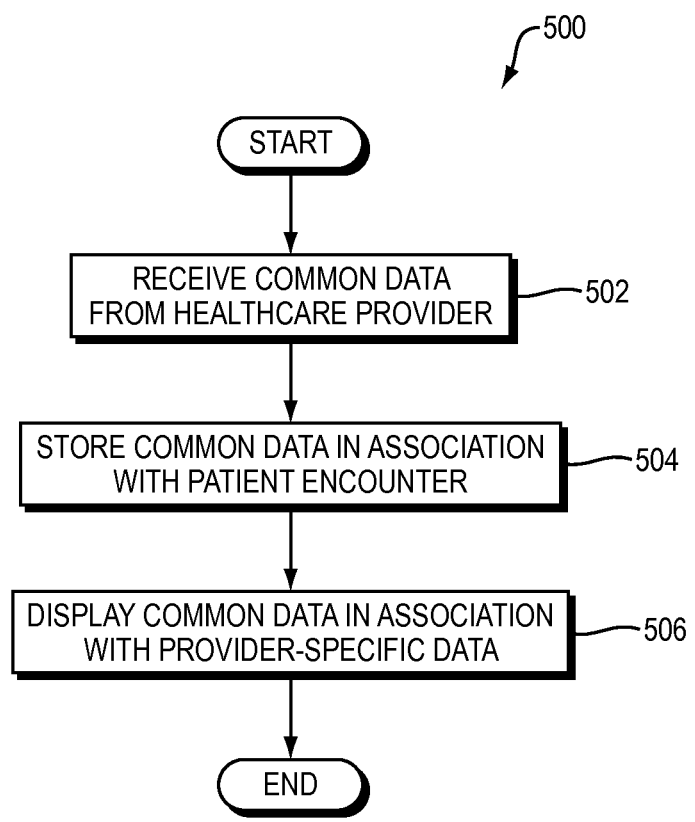
FIG. 5 is a flowchart of a method performed by the system of FIG. 4 according to one embodiment of the present invention.

Referring to FIG. 4, a dataflow diagram is shown of a system 400 for receiving common data from the healthcare providers 104a-c, for storing such common data, and for displaying such common data to the healthcare providers. Referring to FIG. 5, a flowchart is shown of a method 500 performed by the system 400 of FIG. 4 according to one embodiment of the present invention.

The system 400 includes common data 404a-c for a plurality of patients. In particular, common data 404a may be common data for an encounter of patient 106, common data 404b may be common data for another patient (not shown), and common data 404c may be common data for yet another patient (not shown). As will be described in more detail below, common data 404a may include common data received and aggregated from two or more of the healthcare providers 104a-c. In general, the patient data interface 110 may display some or all of patient 106's common data 404a to all of the healthcare providers 104a-c (e.g., in the common data area 304 of the user interface 300) whenever the output 132 is displayed to any of the healthcare providers 104a-c. As a result:

when a first instance of the user interface 300 is displayed to a first one of the healthcare providers 104a-c (e.g., provider 104a) in connection with an encounter of the patient 106, that instance may include both: (1) first provider-specific output (e.g., in the areas 302a-f) that is tailored to the first healthcare provider and related to the patient encounter; and (2) common output representing the common data 404a for the patient 106; and when a second instance of the user interface 300 is displayed to a second one of the healthcare providers 104a-c (e.g., provider 104b) in connection with the same encounter of the patient 106, that instance may include both: (1) second provider-specific output (e.g., in the areas 302a-f) that is tailored to the second healthcare provider and related to the patient encounter; and (2) common output representing the same common data 404a for the patient 106 that was displayed to the first healthcare provider.

In other words, the patient data interface 110 may display different provider-specific output, but the same common data 404a, to the two healthcare providers in connection with the patient encounter.

The system 400 may enable the healthcare providers 104a-c to update the common data 404a in any of a variety of ways. For example, the patient data interface 110 may include a common data module 406. The healthcare provider 104a may provide common data input 402 to the common data module 406 (FIG. 5, operation 502). The healthcare provider 104a may provide the common data input 402 in any of a variety of ways. For example, the common data area 304 may be or include a text field, and the healthcare provider 104a may provide the common data input 402 by typing free-form text into the text field.

The common data module 406 may store the common data input 402 and/or data derived therefrom in the patient 106's common data 404a, such as by appending the common data input 402 to the patient 106's common data 404a, deleting data from the patient 106's common data 404a, or otherwise modifying the patient 106's common data 404 based on the common data input 402 (FIG. 5, operation 504). The common data module 406 may store metadata in association with the common data input 402 in the common data 404a, such as one or more of the identifier 114a of the provider 104a, the current time, the patient identifier 108a, or an identifier of the current encounter of the patient 106.

The common data 404a-c may, for example, be stored in the patient data repository 116 of FIG. 1. For example, the patient 106's common data 404a may be stored within the patient 106's data 118 in the patient data repository 116. Storing the common data input 402, therefore, may include storing the common data input 402 in the patient 106's data 118 in the patient data repository 116 or otherwise updating the patient 106's data 118 in the patient data repository 116 based on the common data input 402.

The patient data interface 110 may display the common data input 402 and/or the updated common data 404a to the healthcare provider 104a, e.g., in the common data area 304 of the user interface 300 (FIG. 5, operation 506). For example, the common data module 406 may receive some or all of the updated patient common data 404a and provide the retrieved common data 408 to the patient data output module 134, which may update the patient output 132 to display the common data 408. The common data 408 may, for example, be part of the patient data 112 in FIG. 1. For example, the common data area 304 may include a list of all previous common data input (including common data input 402) provided by the healthcare provider 104a and the other healthcare providers 104b-c in connection with the current encounter of the patient 106. Such a list may be displayed in any manner, such as in reverse chronological order.

Although the system 400 and method 500 are illustrated in connection with common data input 402 received from the healthcare provider 104a, the system 400 and method 500 may be performed additionally in connection with other common data input (not shown) received from any one or more of the other healthcare providers 104b-c, to thereby further update the patient 106's common data 404a based on such additional common data input. As a result, whenever the patient output 132 (e.g., the user interface 300 of FIG. 3) is displayed to any of the healthcare providers 104a in connection with the current encounter of the patient 106, such output 132 will include or otherwise reflect some or all of the common data input provided by all some or all of the healthcare providers 104a-c in connection with that encounter of the patient 106, in combination with provider-specific output that is relevant to the healthcare provider to whom the output 132 is displayed.

Although certain embodiments described above are described as using preconfigured rules or other preconfigured steps to generate the data displayed in the various summary areas 302a-f, this is merely an example and does not constitute a limitation of the present invention. Embodiments of the present invention are not limited to using a fixed set of techniques to generate data in the summary areas 302a-f, but instead may adapt the techniques used to generate such summaries in response to behavior of the user 104a (and of other users 104b-c) over time.

Figure 6:
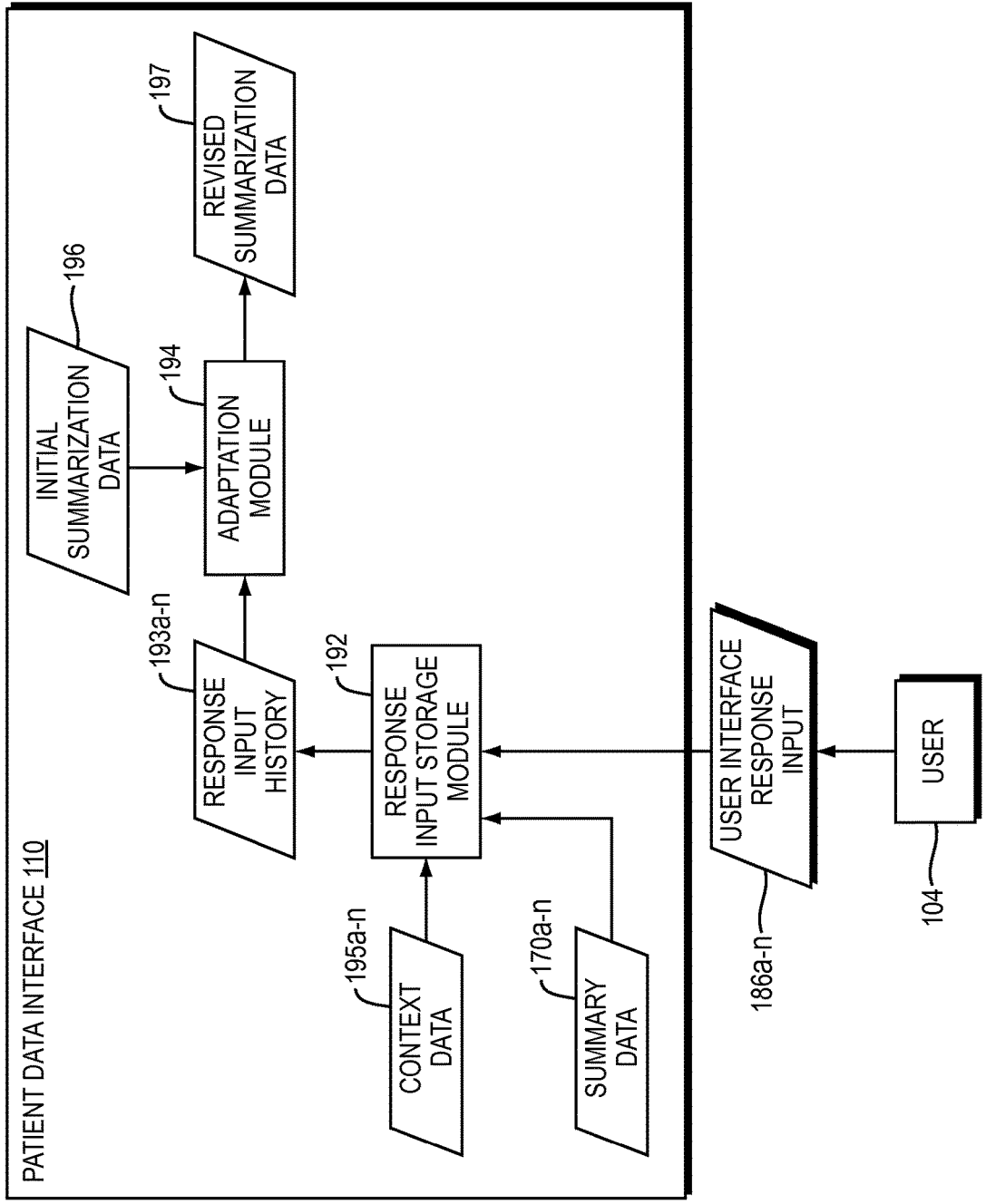
FIG. 6 is a dataflow diagram of a system for adapting the patient data interface of FIGS. 1 and 4 according to one embodiment of the present invention.
Figure 7:
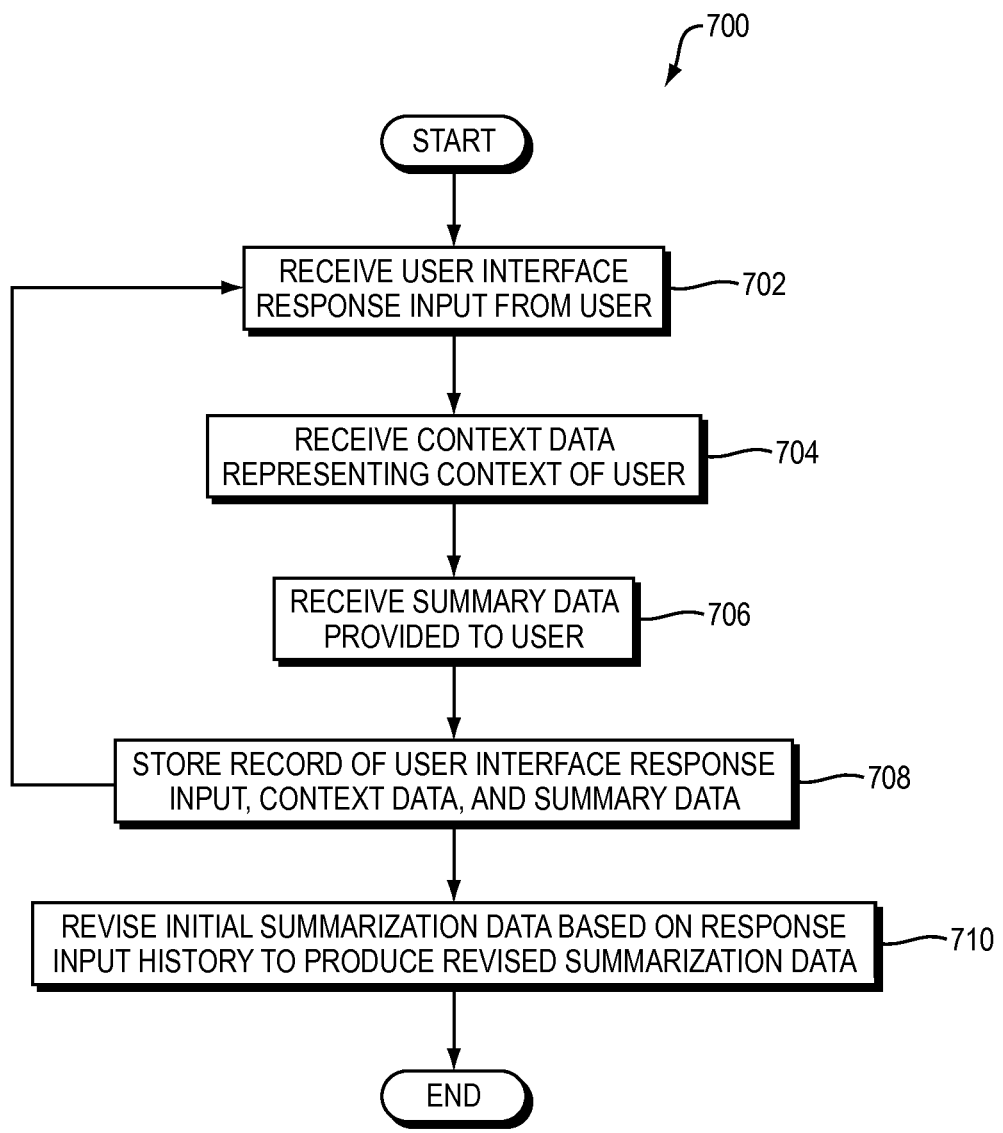
FIG. 7 is a flowchart of a method for performed by the patient data interface of FIG. 6 according to one embodiment of the present invention.

For example, referring to FIG. 6, a dataflow diagram is shown of a system for adapting the patient data interface 110 over time in response to behavior of the user 104 and of other users (such as users 104b and 104c). Referring to FIG. 7, a flowchart is shown of a method 700 performed by the system of FIG. 6 according to one embodiment of the present invention.

As described above, the patient data interface 110 may use any of a variety of techniques to generate the patient output 132 that is provided to the user 104a (such as the output in the summary areas 302a-f shown in FIG. 3). For example, the patient data interface 110 may use a set of rules to generate the patient output 132. The term "summarization data" will be used herein to refer to the data (e.g., rules) that the patient data interface 110 uses to generate the patient output 132. As shown in FIG. 6, the patient data interface 110 may include an initial set of such summarization data 196, which the patient data interface 110 may use initially to perform the functions described above. In general, the system of FIG. 6 and the method 700 of FIG. 7 may be used to revise the initial summarization data 196 based on one or more inputs 186a-n received from the user 104a (and possibly from other users) and the contexts 195a-n in which such inputs 186a-n were received, to generate revised summarization data 197. The patient data interface 110 may then apply the techniques of FIGS. 1-5 to the revised summarization data 197.

More specifically, the patient data interface 110 may obtain a first response input 186a from the user 104a (FIG. 7, operation 702). The response input 186a (and any of the other response inputs 186b-n) may be any input received from the user 104a in connection with the user interface 300. In particular, the response input 186a may be input indicating, directly or indirectly, that the user 104a considers content within a particular element in the user interface (such as one of the summary areas 302a-f, or a portion thereof) is relevant or irrelevant to the user.

For example, the user interface 300 may include, in connection with each of one or more elements of the user interface 300 (such as each of the summary areas 302a and the provider-independent data area 304), one or more user interface controls (such as buttons, checkboxes, or menu items) for receiving input from the user 104a indicating the user 104a's conclusion that the content in the corresponding element of the user interface 300 is either relevant or irrelevant to the user 104a. As a particular example, the user interface 300 may include a "thumbs up" button and a "thumbs down" button next to each of the summary areas 302a-f and the provider-independent data area. The user 104a may click on the "thumbs up" button next to one of the areas 302a-f or 304 to indicate expressly that the user 104a considers the content (e.g., summary) within the corresponding area to be relevant to the user 104a. Conversely, the user 104a may click on the "thumbs down" button next to one of the areas 302a-f or 304 to indicate that the user 104a considers the content (e.g., summary) within the corresponding area to be irrelevant to the user 104a. Such clicks on the "thumbs up" and "thumbs down" buttons are examples of the user interface response input 186a-n.

The user 104a may provide a variety of input through the user interface 300. For example, the user 104a may provide input to scroll through content in the areas 302a-f and 304, input to expand and collapse hierarchical content in the areas 302a-f and 304, select content in the areas 302a-f and 304, and copy/paste content in the areas 302a-f and 304. Although the user 104a may not provide such input with the express intent of indicating that the corresponding content is relevant or irrelevant to the user 104a, the patient data interface 110 may treat such inputs, all of which are examples of the user 104a interacting with particular content, as instances of the user interface response inputs 186a-n shown in FIG. 6, and infer the relevance or irrelevance of the corresponding content to the user 104a from such inputs. For example, if the user 104a never expands particular hierarchical content, the patient data interface 110 may infer that such lack of expansion input indicates that the user 104a does not consider such content to be relevant to the user 104a. As another example, if the user 104a frequently scrolls through particular content, the patient data interface 110 may infer that the user 104a considers such content to be relevant to the user 104a.

The patient data interface 110 may also receive context data 195a representing a current context of the user 104a (e.g., a context of the user 104a at the time when the user 104 provides the user interface response input 186a) (FIG. 7, operation 704). The context data 195a may include any data representing a context of the user 104a, such as data representing the user 104's identity (e.g., real name or username) and/or role (e.g., physician, nurse, billing coder), the organization (e.g., hospital, department) in which the user 104 works, and the current date and/or time of day.

The patient data interface 110 may also receive the patient output 132a (shown in FIG. 7 as summary data 170a) that was provided to the user 104a within the context represented by the context data 195a (FIG. 7, operation 706).

The response input storage module 192 stores a record of the user interface response input 186a, the corresponding context data 195a, and the corresponding summary data 170a in a response input history 193a (FIG. 7, operation 708).

Operations 702-708 of FIG. 7 may be repeated any number of times to store any number of records 193a-n of response inputs 186a-n and corresponding context data 195a-n and summary data 170a-n from the user 104a (and possibly from other users). The response input history records 193a-n may include discrete records of the individual response inputs 186a-n and corresponding context data 195a-n and summary data 170a-n. Additionally, or alternatively, the response input storage module 192 may derive data from the response inputs 186a-n, context data 195a-n, and summary data 170a-n, and store such derived data, such as aggregate data and other statistics, in the response input history records 193a-n.

The system of FIG. 6 may also include an adaptation module 194, which may adapt the initial summarization data 196 based on the response input history 193a-n to produce revised summarization data 197 (FIG. 7, operation 710). The revised summarization data 197 may take any of a variety of forms, such as a set of revised rules which differ from the initial rules represented by the initial summarization data 196, a revised neural network which differs from an initial neural network represented by the initial summarization data 196, or a revised set of statistical classifiers which differ from an initial set of statistical classifiers represented by the initial summarization data 196. The adaptation module 194 may generate the revised summarization data 197 using any of a variety of techniques to generate the revised summarization data 197, such as any technique based on machine learning, neural networks, or statistical classifiers.

For example, if the response input history 193a-n indicates that the user 104a (and possibly other users) tends to find content in a particular area of the user interface 300 to be relevant in a particular context (or a particular set of related contexts), then the adaptation module 194 may revise the initial summarization data 196 to indicate, in the revised summarization data 197, that the same or similar content should continue to be included in summaries that are generated and presented to the user 104a (and possibly other users) in the user interface 300 in the same and similar contexts in the future, and possibly that such content should be emphasized to such users 104, such as by modifying its formatting to emphasize such content (e.g., by displaying it in bold, underlining it, changing its color, or increasing its font size) or by modifying the spatial location of such content to emphasize it (e.g., by displaying it higher in one of the areas 302a-f or 304 than previously).

As another example, if the response input history 193a-n indicates that the user 104a (and possibly other users) tends to content in a particular area of the user interface 300 to be irrelevant in a particular context (or a particular set of related contexts), then the adaptation module 194 may revise the initial summarization data 196 to indicate, in the revised summarization data 197, that the irrelevant content should not be included in summaries that are generated and presented to the user 104a (and possibly other users) in the user interface 300 in the same and similar contexts in the future, or instead that such content should be deemphasized to such users, such as by modifying its formatting to emphasize such content (e.g., by displaying it in plain text, changing its color, or decreasing its font size) or by modifying the spatial location of such content to de-emphasize it (e.g., by displaying it lower in one of the areas 302a-f or 304 than previously).

Regardless of the particular manner in which the adaptation module 194 adapts the initial summarization data 196 to produce the revised summarization data 197, once the revised summarization data 197 have been produced, the patient data interface 110 may apply the revised summarization data 197 to the techniques disclosed herein in connection with FIGS. 1-5 to generate future summaries in the user interface 300 in accordance with the revised summarization data 197 and to provide such summaries to the user 104a (and possibly to other users). Furthermore, the method 700 of FIG. 7 may be performed any number of times to further revise the revised summarization data 197 any number of times based on new response inputs, context data, and summary data once they have been generated.

Although certain embodiments of the present invention are disclosed herein as displaying user-generated content (such as physicians' notes or other common data input 402) in the provider-independent data area 304, this is merely an example and does not constitute a limitation of the present invention. Alternatively or additionally, the patient data interface 110 may automatically generate and display content within the provider-independent data area 304. As a result, the terms "provider-independent data" and "common data," as used herein, may refer to data which includes (in whole or in part) automatically-generated data.

Figure 8:
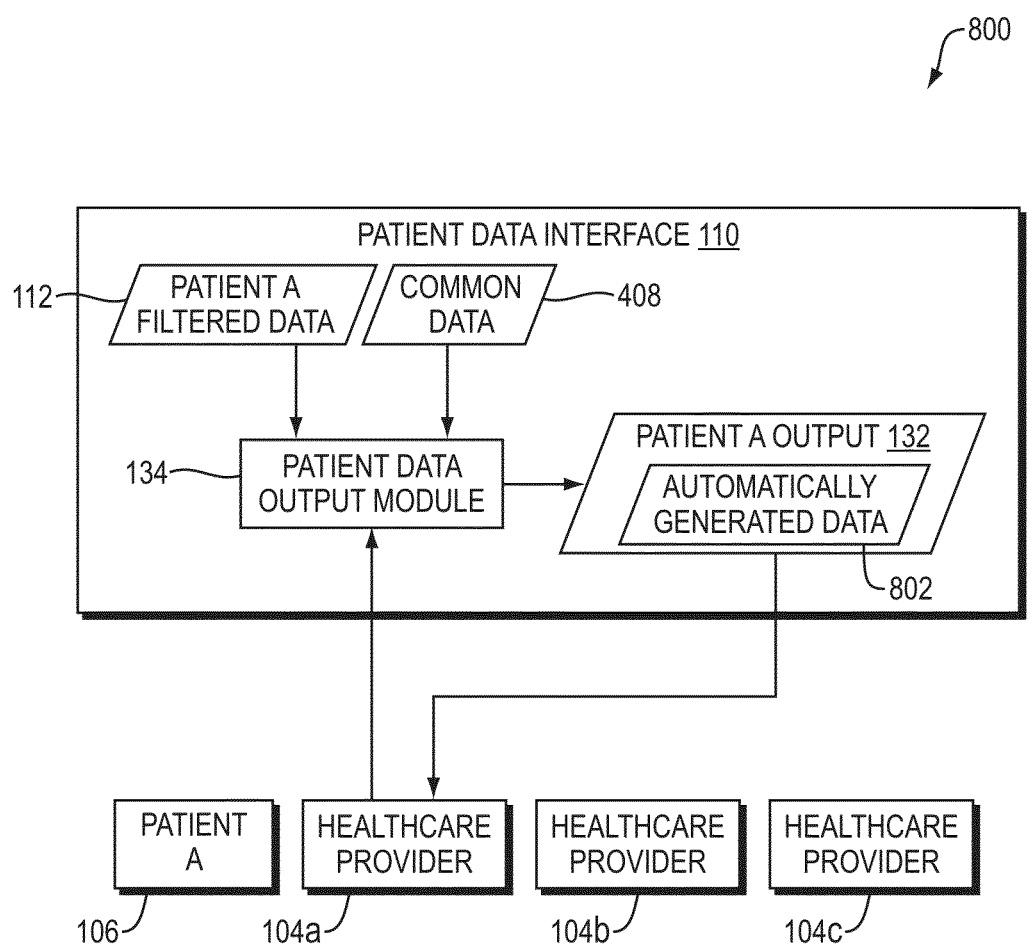
FIG. 8 is a dataflow diagram of a system for generating and displaying patient information automatically according to one embodiment of the present invention.
Figure 9:
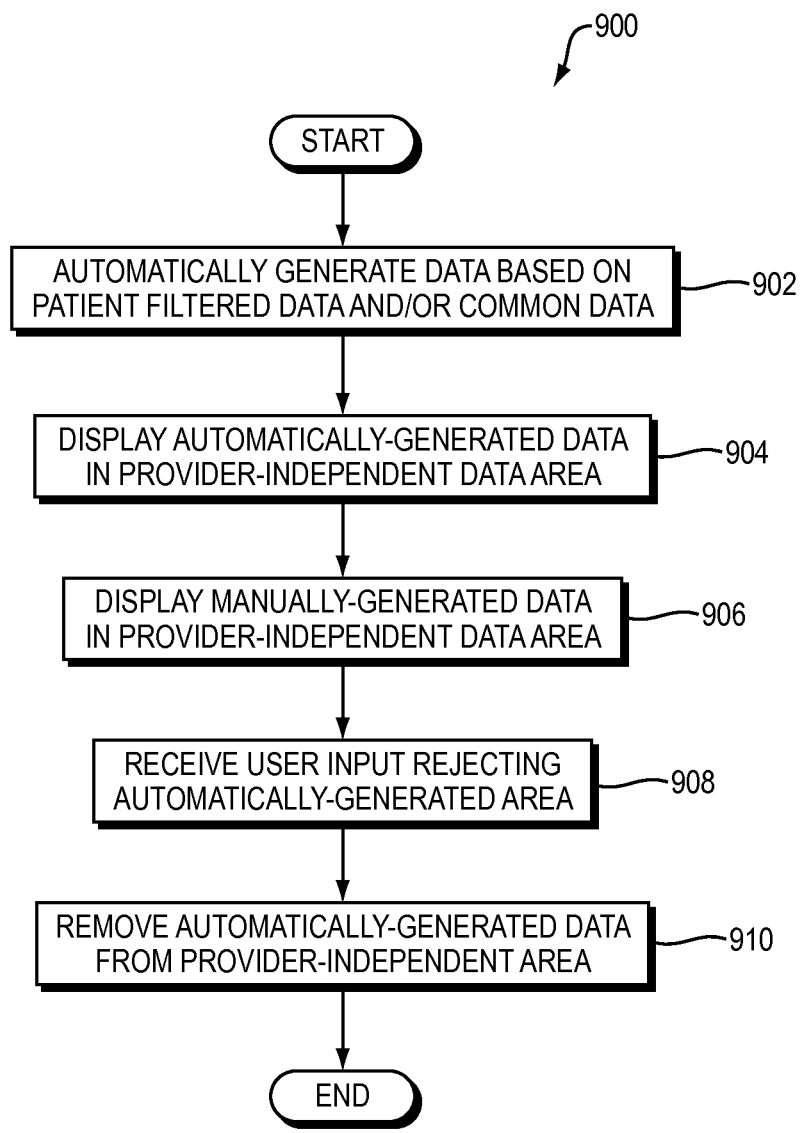
FIG. 9 is a flowchart of a method performed by the system of FIG. 8 according to one embodiment of the present invention.

For example, referring to FIG. 8, a dataflow diagram is shown of a system 800 for automatically-generated data 802 based on one or more of the patient filtered data 112 and the common data 408 according to one embodiment of the present invention. Referring to FIG. 9, a flowchart is shown of a method 900 performed by the system 800 of FIG. 8 according to one embodiment of the present invention. The system 800 of FIG. 8 may include some or all of the elements of the system 100 of FIG. 1 and/or the system 400 of FIG. 4. Some elements of FIGS. 1 and 4, however, are omitted from FIG. 8 merely for ease of illustration.

The patient data interface 110 may, for example, automatically-generated content 802 based on one or both of the patient filtered data 112 and the common data 408 (FIG. 9, operation 902). The patient data interface 110 may display, in the provider-independent data area 304, either: (1) solely the automatically-generated content 802 (FIG. 2, operation 904); or (2) both the automatically-generated content 802 and manually-entered content (e.g., the common data 408, or data derived therefrom as described above) (FIG. 2, operations 904 and 906). As a result, the provider-independent data area 304 may include manually-entered data (such as the manually-entered data described above in connection with FIGS. 4 and 5), automatically-generated data 802, or a combination thereof.

It may be useful for the user 104a to be able to distinguish between manually-generated data and automatically-generated data 802 in the provider-independent data area 304. To achieve this result, the patient data interface 110 may include, in the display of the automatically-generated data 802 in the provider-independent data area 304, a visual indication that the automatically-generated data 802 was generated automatically, such as by displaying a particular icon in or near the display of the automatically-generated data 802, formatting the display of the automatically-generated data 802 to indicate that it was generated automatically (such as by displaying it in boldface or in a special font or color), or spatially arranging the display of the automatically-generated data 802 to indicate that it was generated automatically (such as by grouping all automatically-generated data 802 together or by locating some or all of the automatically-generated data 802 above, below, to the left, or to the right of manually-generated data).

Additionally or alternatively, the patient data interface 110 may apply any of the techniques described in the preceding paragraph to indicate that any manually-generated data in the provider-independent data area 304 was generated manually. For example, the patient data interface 110 may display a first icon next to any automatically-generated content 802 and display a second icon next to any manually-generated content, where the second icon differs from the first icon. More generally, the patient data interface 110 may use formatting or any other tailoring of the visual displays of automatically-generated data 802 and manually-generated data to indicate that the former was generated automatically and that the latter was generated manually.

The automatically-generated data 802 may be generated, for example, based on one or more of the summaries in the summary areas 302a-f in FIG. 3 and/or the manually-entered common data in the provider-independent data area 304. In general, the patient data output module 134 may generate the automatically-generated data 802 to include information which is predicted to be important for the users 104a-c to review. For example, the patient data output module 134 may generate the automatically-generated data 802 in a form that is similar to the form that a physician would generate manually, such as a phrase or sentence expressed in a natural language. Such data may include, for example, time-critical notes intended to assist the physician and other healthcare providers in monitoring the patient and/or containing information about key patient conditions which require attention.

The automatically-generated data 802 may include either one or both of structured data and unstructured data. Examples of structured data include data having discrete values, encoded concepts, and contents of fields in EHRs or database records. Examples of unstructured data include free-form text, such as sentences expressed in a natural language (e.g., "please monitor the patient's glucose level").

The patient data interface 110 may enable the user 104a to accept or reject the automatically-generated data 802, in whole or in part. For example, FIG. 9 illustrates an embodiment in which the patient data output module 134 first displays the automatically-generated data 802 within the provider-independent data area 304, and then enables the user 104a (or any of the other users 104c) to provide input rejecting the automatically-generated data 802 (FIG. 9, operation 908). Such input may take any form, such as clicking on a "Reject" button located near the display of the automatically-generated data 802. In response to receiving such rejection input, the patient data interface 110 may remove the display of the automatically-generated data 802 from the provider-independent data area 304 (FIG. 9, operation 910).

Additionally or alternatively (although not shown in FIG. 9), the patient data interface 110 may first prompt the user 104a to accept or reject the automatically-generated data 802 before displaying the automatically-generated data 802 in the provider-independent data area 304. In response to such a prompt, the user 104a may provide input indicating either acceptance or rejection of the automatically-generated data 802 (such as by clicking on an "Accept" button or a "Reject" button). If the user 104a's input indicates acceptance of the automatically-generated data 802, then the patient data interface 110 may display the automatically-generated data 802 within the provider-independent data area 304. Otherwise, the patient data interface 110 may not display the automatically-generated data 802 within the provider-independent data area 304.

Such "opt out" and "opt in" approaches may be combined with each other. For example, the patient data interface 110 may first require the user 104a to accept the automatically-generated data 802 before displaying that data 802 in the provider-independent data area 304 (i.e., opt in). After displaying such data 802 within the provider-independent data area, the patient data interface 110 may enable the user 104a (and other users 104b-c) to provide additional input rejecting the automatically-generated data 802, thereby causing the patient data interface 110 to remove the automatically-generated data 802 from the provider-independent data area 304.

Although the techniques disclosed in connection with FIGS. 8 and 9 are described above as being used to generate data automatically for display in the provider-independent data area 304, this is not a limitation of the present invention. More generally, embodiments of the present invention may use any of the techniques disclosed above to automatically-generate and display data in any of the summary areas 302a-f. Any of the other techniques disclosed herein in connection with the automatically-generated data 802, such as the techniques for user acceptance and rejection of such data 802, may be applied to automatically-generated data in any of the summary areas 302a-f.

Embodiments of the present invention have a variety of advantages, such as the following. One advantage of embodiments of the present invention is that they provide a quick, easy, and user-friendly way for physicians and other healthcare providers to input and share information that is relevant to a specific patient and/or patient encounter, such as their impressions of the patient's current needs, with each other. In particular, healthcare providers may supplement the common data associated with a particular patient encounter quickly and easily, such as by typing text into a text field, without needing to obtain approval or sign-off on such text, or otherwise to follow the verification procedures that typically are required to commit data to a patient's EHR. As a result, embodiments of the present invention may not only reduce the amount of time required for healthcare providers to input such common data, but also increase the likelihood that they will input such data, and do so immediately, rather than forego inputting such data due to the burden of inputting data into a conventional EHR. In particular, healthcare providers may input common data representing their current concerns about the patient (e.g., "please monitor the patient's blood glucose level") in an effort to communicate those concerns to other healthcare professionals associated with the patient's encounter, and thereby increase the likelihood that such concerns will be made known among all of the healthcare professionals associated with the patient's encounter, without requiring each healthcare professional to write a full summary of the patient encounter. Instead, each healthcare professional may merely input new information in the common data (such as a new concern), without needing to copy or otherwise repeat old data, because such existing data is already readily available to all of the healthcare professionals associated with the patient encounter via the patient output 132 (e.g., the areas 302a and the common data area 304). As a result, the healthcare professionals associated with a patient encounter may use the encounter's common data as a mechanism for quickly and easily communicating recent concerns and other information with each other.

Furthermore, once any healthcare provider has input common data for a patient encounter, embodiments of the present invention may provide that common data automatically to that healthcare provider and other healthcare providers associated with the same patient encounter, such as by displaying such common data in the common data area 304 of the user interface 300 shown in FIG. 3. The healthcare providers 300 need not search for the common data. Instead, embodiments of the present invention present such common data directly and clearly to the healthcare providers, thereby increasing the usefulness of the common data in the process of providing healthcare services to the patient.

Furthermore, embodiments of the present invention present the common data in combination with other data related to the same patient encounter, such as data copied or otherwise derived from any of a variety of existing data sources related to the patient encounter, such as the patient's EHR. For example, the user interface of FIG. 3 presents both a patient's common data and other data related to the patient's current encounter. In this way, embodiments of the present invention provide healthcare professionals with a variety of information about the patient's current encounter in a single display, thereby eliminating or reducing the need for healthcare professionals to search or otherwise navigate through multiple sources of data to obtain information that is relevant to them in relation to the patient encounter.

Moreover, embodiments of the present invention automatically tailor at least some of the output 132 that is provided to each healthcare professional to that healthcare professional, e.g., based on the medical practice area and/or role of that healthcare professional in the encounter of the patient. Tailoring such information provides a significant benefit over existing systems, which display the same information to all healthcare professionals involved in a patient encounter, despite the fact that different information is relevant to different healthcare professionals. As a result, existing systems, which often include large volumes of highly-detailed information related to a patient encounter, present all such data to every healthcare professional involved in the patient encounter, and put the burden of searching through such information to find relevant information on each healthcare provider. In contrast, embodiments of the present invention automatically tailor the information presented to each healthcare provider to the characteristics of that healthcare provider, such as by re-ordering such information, filtering such information to remove irrelevant information, and/or emphasizing portions of such information, thereby reducing the cognitive load on each healthcare provider, decreasing the amount of time spent by each healthcare provider searching for relevant information, and increasing the likelihood that each healthcare provider will find relevant information. In all of these ways, embodiments of the present invention facilitate the process of enabling each healthcare provider to provide quality healthcare services to the patient.

Although the common data associated with a patient encounter may be informal and need not be committed to the patient data repository 116 according to the formal procedures required to commit data to the repository 116, some or all of the common data associated with a patient encounter may be committed to the patient data repository. For example, data in the patient 106's common data 404*a* may be committed to the patient 106's data 118 in the repository 116 in response to a trigger, such as input from one of the healthcare professionals representing an instruction to commit some or all of the common data 404*a* to the patient 106's data 118 in the repository 116, or after some minimum amount of time has passed. Data in the common data 404*a* may be committed to the patient 106's data 118 in the repository in any of a variety of ways. For example, concepts in the common data 404*a* may be recognized and encoded using any of the techniques disclosed in U.S. Pat. No. 7,584,103 B2, issued on Sep. 1, 2009, entitled, "Automated Extraction of Semantic Content and Generation of a Structured Document From Speech"; and/or U.S. Pat. No. 7,716,040 B2, issued on May 11, 2010, entitled, "Verification of Extracted Data," both of which are hereby incorporated by reference herein. Such encoded concepts may then be stored in the patient 106's data 118, and (optionally) deleted from the common data 404*a*. In general, any time data from the common data 404*a* are committed to (stored in) the repository 116, any procedures required for committing data to the repository 116 may be followed, such as requiring that the healthcare professional responsible for creating and/or committing the data review, verify, and sign off on the committed data in compliance with any applicable legal, regulatory, and/or institutional requirements.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

For example, although certain embodiments of the present invention are described as used in the context of a hospital, this is merely an example and does not constitute a limitation of the present invention. For example, the Affordable Care Act has created organizations known as Accountable Care Organizations (ACOs), which are conglomerations of health providers, such as physicians' offices, hospitals, nursing homes, and care givers. An ACO is responsible for the health of a population of patients. Under the ACA, the patients within an ACO are tracked across the various health providers, and their care is coordinated through a central coordination center. Embodiments of the present invention may be used by such central coordination centers. This is merely another example of a context in which embodiments of the present invention may be used.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

What is claimed is:

1. A method for automatically modifying graphical user interface output based on response input associated with output including common data and filtered and modified patient data, the method performed by at least one computer processor executing computer program instructions stored on at least one non-transitory computer-readable medium, the method comprising:
   (A) identifying an identifier of a patient;
   (B) retrieving from within first patient data related to the patient in a repository, based on the identifier of the patient, first filtered patient data;
   (C) identifying a first identifier of a first user;
   (D) after (B) and before (F), automatically prioritizing the first filtered patient data based on the first identifier of the first user to produce first modified patient data,
   (E) retrieving common data from the repository based on the identifier of the patient, wherein the common data is received, in the repository, from at least the first user and a second user;
   (F) providing first output, to the first user, through a graphical user interface, the first output representing the first modified patient data within a first area of the graphical user interface and the retrieved common data within a second area of the graphical user interface, the first area being separated from the second area;
   (G) identifying a second identifier of a second user;
   (H) retrieving, from within the first patient data in the repository, based on the identifier of the patient, second filtered patient data;
   (I) after (H) and before (J), automatically prioritizing the second filtered patient data based on the second identifier of the second user to produce second modified patient data, wherein the first modified patient data differs from the second modified patient data;
   (J) providing second output, to the second user, through the graphical user interface, the second output representing the second modified patient data within the first area of the graphical user interface and the retrieved common data within the second area of the graphical user interface;
   (K) receiving, from the first user, first user interface response input in connection with the output comprising the first modified patient data and the common data; and
   (L) providing modified second output to the second user, responsive to the received first user interface response input.

2. The method of claim 1, further comprising:
   (M) receiving, from the first user, first free-form text input; and
   (N) updating the patient data based on the first free-form text input to produce updated patient data.

3. The method of claim 2, further comprising:
   (O) providing third output, to the first user, representing the updated patient data.

4. The method of claim 2, further comprising:
   (O) providing third output, to the second user, representing the updated patient data.

5. The method of claim 1, further comprising:
   (M) receiving, from the first user, first free-form text input;
   (N) updating the common data in the repository based on the first free-form text input to produce updated common data.

6. The method of claim 5, further comprising:
   (O) providing third output, to the first user, representing the updated common data; and
   (P) providing fourth output, to the second user, representing the updated common data.

7. The method of claim 1, wherein the first filtered patient data comprises data describing an encounter of the patient, wherein the encounter comprises at least one of an examination, a hospital stay, a medical procedure, and an appointment.

8. The method of claim 7, wherein the data describing the encounter of the patient comprises a clinical note describing the encounter of the patient.

9. The method of claim 7, wherein the data describing the encounter of the patient comprises encoded concepts.

10. the method of claim 1, wherein (D) comprises re-ordering data within the first filtered patient data based on the first identifier of the first user.

11. The method of claim 1, wherein (D) comprises summarizing data within the first filtered patient data based on the first identifier of the first user.

12. The method of claim 1, wherein (D) comprises filtering data within the first filtered patient data based on the first identifier of the first user.

13. The method of claim 1, wherein (D) comprises emphasizing data within the first filtered patient data based on the first identifier of the first user.

14. The method of claim 1:
wherein (D) comprises:
(D) (1) identifying a first relevance criterion based on the first identifier of the first user;
(D) (2) determining whether a first portion of the first filtered patient data satisfies the first relevance criterion; and
(D) (3) before (F), modifying the first portion of the first patient data based on the first identifier of the first user if the first portion of the first filtered patient data is determined to satisfy the first relevance criterion; and
wherein (I) comprises:
(I) (1) identifying a second relevance criterion based on the second identifier of the second user, wherein the second relevance criterion differs from the first relevance criterion;
(I) (2) determining whether a second portion of the first filtered patient data satisfies the second relevance criterion; and
(I) (3) before (J), modifying the second portion of the first filtered patient data based on the second identifier of the second user if the second portion of the first filtered patient data is determined to satisfy the second relevance criterion.

15. The method of claim 1, further comprising:
(M) identifying second patent data related to the patient based on the identifier of the patient and the first user interface response input.

16. The method of claim 1, wherein the first user interface response input comprises input indicating expressly that the first user considers a portion of the first modified patient data to be relevant to the first user.

17. The method of claim 1, wherein the first user interface response input comprises input indicating expressly that the first user considers a portion of the first modified patient data to be irrelevant to the first user.

18. The method of claim 1, wherein the first user interface response input comprises input representing an interaction of the first user with a portion of the first modified patient data.

19. The method of claim 1, wherein the first user interface response input comprises input selecting a portion of the first modified patient data.

20. The method of claim 1, further comprising:
(M) automatically generating, based on the first modified patient data, automatically generated common data;
(N) providing output, to the first user, representing the automatically generated common data; and
(O) providing output, to the second user, representing the automatically generated common data.

21. The method of claim 1, further comprising:
(M) automatically generating, based on the common data, automatically generated common data;
(N) providing output, to the first user, representing the automatically generated common data; and
(O) providing output, to the second user, representing the automatically generated common data.

22. The method of claim 1, further comprising:
(M) automatically generating, based on the first modified patient data and the retrieved common data, automatically generated data; and
(N) providing output, to the first user, representing the automatically generated data.

23. A system comprising at least one non-transitory computer-readable medium having computer program instructions stored thereon, wherein the computer program instructions are executable by at least one computer process to perform a method for automatically modifying graphical user interface output based on response input associated with output including common data and filtered and modified patient data, the method, the method comprising:
(A) identifying an identifier of a patient;
(B) retrieving, from within first patient data related to the patient in a repository, based on the identifier of the patient, first filtered patient data;
(C) identifying a first identifier of a first user;
(D) after (B) and before (F), automatically prioritizing the first filtered patient data based on the first identifier of the first user to produce first modified patient data;
(E) retrieving common data from the repository based on the identifier of the patient, wherein the common data is received, in the repository, from at least the first user and a second user;
(F) providing first output, to the first user, through a graphical user interface, the first output representing the first modified patient data within a first area of the graphical user interface and the retrieved common data within a second area of the graphical user interface, the first area being separated from the second area;
(G) identifying a second identifier of a second user;
(H) retrieving, from within the first patient data in the repository, based on the identifier of the patient, second filtered patient data;
(I) after (H) and before (J), automatically prioritizing the second filtered patient data based on the second identifier of the second user to produce second modified patient data, wherein the first modified patient data differs from the second modified patient data;
(J) providing second output, to the second user, through the graphical user interface, the second output representing the second modified patient data within the first area of the graphical user interface and the retrieved common data within the second area of the graphical user interface;
(K) receiving, from the first user, first user interface response input in connection with the output comprising the first modified patient data and the common data;
(L) providing modified second output to the second user, responsive to the received first user interface response input.

24. The system of claim 23, wherein the method further comprises:
(M) receiving, from the first user, first free-form text input; and
(N) updating the first patient data based on the first free-form text input to produce updated patient data.

25. The system of claim 24, wherein the method further comprises:
(O) providing third output, to the first user, representing the updated patient data.

26. The system of claim 24, wherein the method further comprises:
(O) providing third output, to the second user, representing the updated patient data.

27. The system of claim 23, wherein the method further comprises:
(M) receiving, from the first user, first free-form text input;
(N) updating the common data based on the first free-form text input to produce updated common data.

28. The system of claim 27, wherein the method further comprises:
 (O) providing third output, to the first user, representing the updated common data; and
 (P) providing fourth output, to the second user, representing the updated common data.

29. The system of claim 23, wherein the first filtered patient data comprises data describing an encounter of the patient, wherein the encounter comprises at least one of an examination, a hospital stay, a medical procedure, and an appointment.

30. The system of claim 29, wherein the data describing the encounter of the patient comprises a clinical note describing the encounter of the patient.

31. The system of claim 29, wherein the data describing the encounter of the patient comprises encoded concepts.

32. The system of claim 23, wherein (D) comprises re-ordering data within the first filtered patient data based on the first identifier of the first user.

33. The system of claim 23, wherein (D) comprises summarizing data within the first filtered patient data based on the first identifier of the first user.

34. The system of claim 23, wherein (D) comprises filtering data within the first filtered patient data based on the first identifier of the first user.

35. The system of claim 23, wherein (D) comprises emphasizing data within the first filtered patient data based on the first identifier of the first user.

36. The system of claim 23:
 wherein (D) comprises:
  (D) (1) identifying a first relevance criterion based on the first identifier of the first user;
  (D) (2) determining whether a first portion of the first filtered patient data satisfies the first relevance criterion; and
  (D) (3) before (F), modifying the first portion of the first filtered patient data based on the first identifier of the first user if the first portion of the first patient data is determined to satisfy the first relevance criterion; and
 wherein (I) comprises:
  (I) (1) identifying a second relevance criterion based on the second identifier of the second user, wherein the second relevance criterion differs from the first relevance criterion;
  (I) (2) determining whether a second portion of the first filtered patient data satisfies the second relevance criterion; and
  (I) (3) before (J), modifying the second portion of the first patient data based on the second identifier of the second user if the second portion of the first patient data is determined to satisfy the second relevance criterion.

37. The system of claim 23, wherein the method further comprises:
 (K) identifying second patent data related to the patient based on the identifier of the patient and the first user interface response input.

38. The system of claim 23, wherein the first user interface response input comprises input indicating expressly that the first user considers a portion of the first modified patient data to be relevant to the first user.

39. The system of claim 23, wherein the first user interface response input comprises input indicating expressly that the first user considers a portion of the first modified patient data to be irrelevant to the first user.

40. The system of claim 23, wherein the first user interface response input comprises input representing an interaction of the first user with a portion of the first modified patient data.

41. The system of claim 23, wherein the first user interface response input comprises input selecting a portion of the first modified patient data.

42. The system of claim 23, wherein the method further comprises:
 (M) automatically generating, based on the first modified patient data, automatically generated common data;
 (N) providing output, to the first user, representing the automatically generated common data; and
 (O) providing output, to the second user, representing the automatically generated common data.

43. The system of claim 23, wherein the method further comprises:
 (M) automatically generating, based on the retrieved common data, automatically generated common data;
 (N) providing output, to the first user, representing the automatically generated common data; and
 (O) providing output, to the second user, representing the automatically generated common data.

44. The system of claim 23, wherein the method further comprises:
 (M) automatically generating, based on the first modified patient data and the common data, automatically generated data; and
 (N) providing output, to the first user, representing the automatically generated data.

* * * * *